(12) United States Patent  
Ellis

(10) Patent No.: US 8,819,961 B1
(45) Date of Patent: Sep. 2, 2014

(54) SETS OF ORTHOTIC OR OTHER FOOTWEAR INSERTS AND/OR SOLES WITH PROGRESSIVE CORRECTIONS

(76) Inventor: Frampton E. Ellis, Jasper, FL (US)

( * ) Notice: Subject to any disclaimer, the term of this patent is extended or adjusted under 35 U.S.C. 154(b) by 1255 days.

(21) Appl. No.: 12/163,332

(22) Filed: Jun. 27, 2008

Related U.S. Application Data

(60) Provisional application No. 60/929,485, filed on Jun. 29, 2007, provisional application No. 60/929,663, filed on Jul. 6, 2007, provisional application No. 60/929,672, filed on Jul. 9, 2007, provisional application No. 60/935,555, filed on Aug. 17, 2007.

(51) Int. Cl.
  *A43B 13/24* (2006.01)
  *A61F 5/14* (2006.01)
(52) U.S. Cl.
  USPC ..................... 36/29; 36/43; 36/140
(58) Field of Classification Search
  USPC ......... 36/25 R, 28–29, 31, 43, 114–114, 140, 36/142–144, 165
  See application file for complete search history.

(56) References Cited

U.S. PATENT DOCUMENTS

| | | | | |
|---|---|---|---|---|
| 3,543,765 A | * | 12/1970 | Alzner | 36/147 |
| 4,771,394 A | * | 9/1988 | Cavanagh | 702/160 |
| 5,317,819 A | | 6/1994 | Ellis | |
| 5,544,429 A | | 8/1996 | Ellis | |
| 5,718,063 A | * | 2/1998 | Yamashita et al. | 36/28 |
| 5,909,948 A | | 6/1999 | Ellis | |
| 6,023,857 A | * | 2/2000 | Vizy et al. | 36/30 R |
| 6,038,790 A | * | 3/2000 | Pyle et al. | 36/30 R |
| 6,092,311 A | * | 7/2000 | MacNamara | 36/97 |
| 6,115,941 A | | 9/2000 | Ellis | |
| 6,115,945 A | | 9/2000 | Ellis | |
| 6,163,982 A | | 12/2000 | Ellis | |
| 6,295,744 B1 | | 10/2001 | Ellis | |
| 6,308,439 B1 | | 10/2001 | Ellis | |
| 6,314,662 B1 | | 11/2001 | Ellis | |
| 6,360,453 B1 | | 3/2002 | Ellis | |
| 6,360,457 B1 | * | 3/2002 | Qui et al. | 36/140 |
| 6,408,543 B1 | * | 6/2002 | Erickson et al. | 36/100 |
| 6,487,795 B1 | | 12/2002 | Ellis | |
| 6,584,706 B1 | | 7/2003 | Ellis | |
| 6,591,519 B1 | | 7/2003 | Ellis | |
| 6,609,312 B1 | | 8/2003 | Ellis | |
| 6,629,376 B1 | | 10/2003 | Ellis | |
| 6,662,470 B2 | | 12/2003 | Ellis | |
| 6,668,470 B2 | * | 12/2003 | Ellis, III | 36/25 R |
| 6,675,498 B1 | | 1/2004 | Ellis | |
| 6,675,499 B2 | | 1/2004 | Ellis | |

(Continued)

FOREIGN PATENT DOCUMENTS

WO 2006058013 A2 6/2006

*Primary Examiner* — Winnie Yip
(74) *Attorney, Agent, or Firm* — Mendelsohn, Drucker & Dunleavy, P.C.

(57) ABSTRACT

A footwear sole or an orthotic or combinations of both including a set of incrementally different inserts forming a progressive sequence. The progressive sequence includes inserts having corrective structures that are incrementally closer to a final corrective structure than a corrective structure of a previous insert in the sequence. The corrective structure of the inserts may change in one or more of shape, thickness and firmness of at least one portion of the at least one insert as compared to the previous insert in the sequence. Each of the inserts of the set is worn for a period of time in order of the progressive sequence as part of the footwear sole and/or orthotic.

30 Claims, 14 Drawing Sheets

(56) References Cited

U.S. PATENT DOCUMENTS

| | | | | |
|---|---|---|---|---|
| 6,708,424 | B1 * | 3/2004 | Ellis, III | 36/25 R |
| 6,722,059 | B2 * | 4/2004 | Robinson et al. | 36/29 |
| 6,729,046 | B2 | 5/2004 | Ellis | |
| 6,748,674 | B2 | 6/2004 | Ellis | |
| 6,763,616 | B2 | 7/2004 | Ellis | |
| 6,789,331 | B1 | 9/2004 | Ellis | |
| 6,796,056 | B2 * | 9/2004 | Swigart | 36/29 |
| 6,810,606 | B1 | 11/2004 | Ellis | |
| 6,880,266 | B2 * | 4/2005 | Schoenborn et al. | 36/28 |
| 6,918,197 | B2 | 7/2005 | Ellis | |
| 6,990,756 | B1 * | 1/2006 | Johnson | 36/155 |
| 7,010,869 | B1 | 3/2006 | Ellis | |
| 7,082,697 | B2 | 8/2006 | Ellis | |
| 7,093,379 | B2 | 8/2006 | Ellis | |
| 7,174,658 | B2 | 2/2007 | Ellis | |
| 7,200,955 | B2 * | 4/2007 | Foxen | 36/25 R |
| 7,234,249 | B2 | 6/2007 | Ellis | |
| 7,249,425 | B2 * | 7/2007 | Wang | 36/29 |
| 7,287,341 | B2 | 10/2007 | Ellis | |
| 7,334,350 | B2 | 2/2008 | Ellis | |
| 7,334,356 | B2 | 2/2008 | Ellis | |
| 7,546,699 | B2 * | 6/2009 | Ellis, III | 36/103 |
| 7,721,467 | B2 * | 5/2010 | Cheskin et al. | 36/44 |
| 2002/0050080 | A1 * | 5/2002 | Vasyli | 36/145 |
| 2004/0181971 | A1 * | 9/2004 | Turkbas et al. | 36/44 |
| 2007/0271817 | A1 | 11/2007 | Ellis | |
| 2008/0000108 | A1 | 1/2008 | Ellis | |
| 2008/0005931 | A1 | 1/2008 | Ellis | |
| 2008/0022556 | A1 | 1/2008 | Ellis | |
| 2008/0086916 | A1 | 4/2008 | Ellis | |

* cited by examiner

145

↑
700

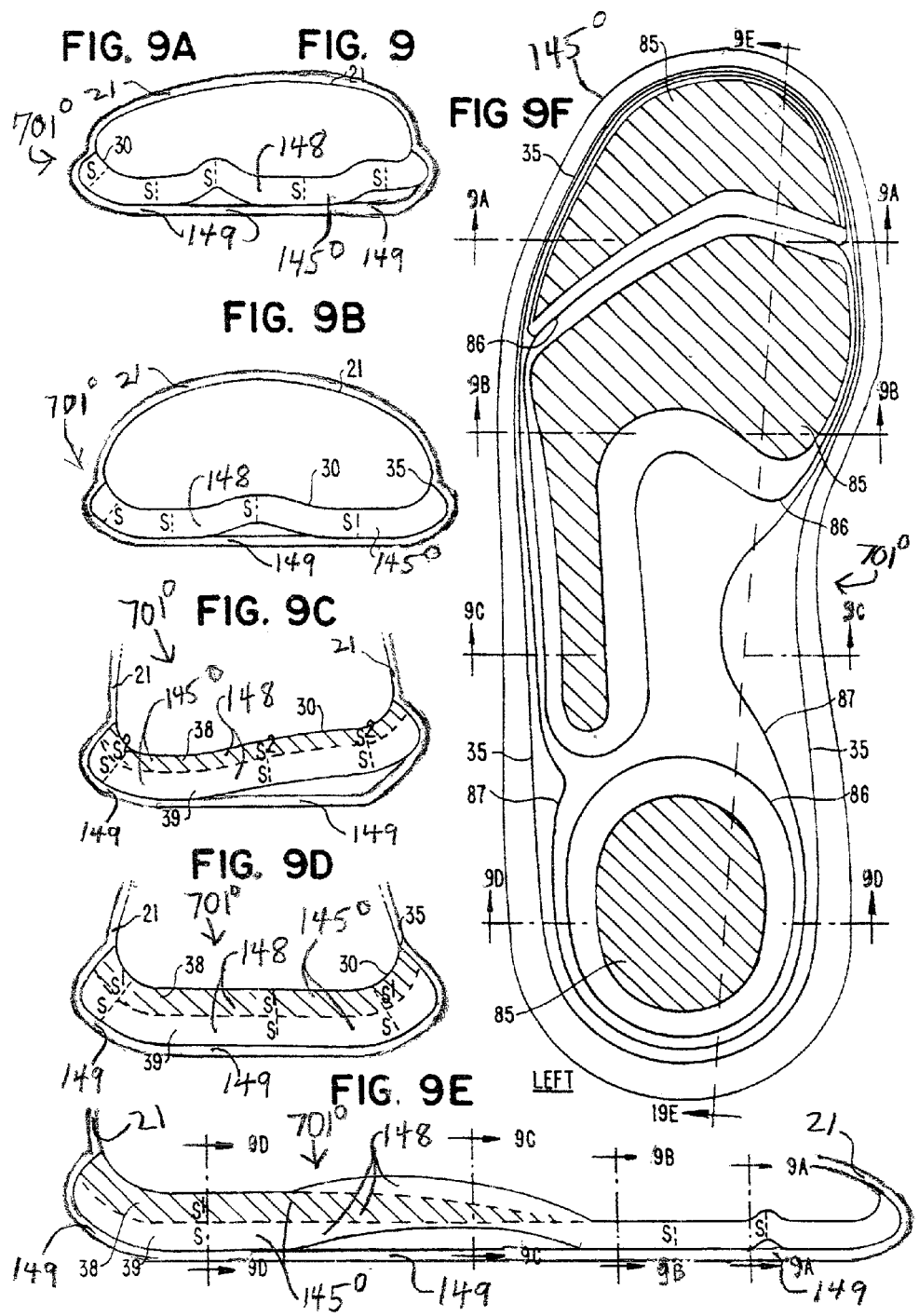

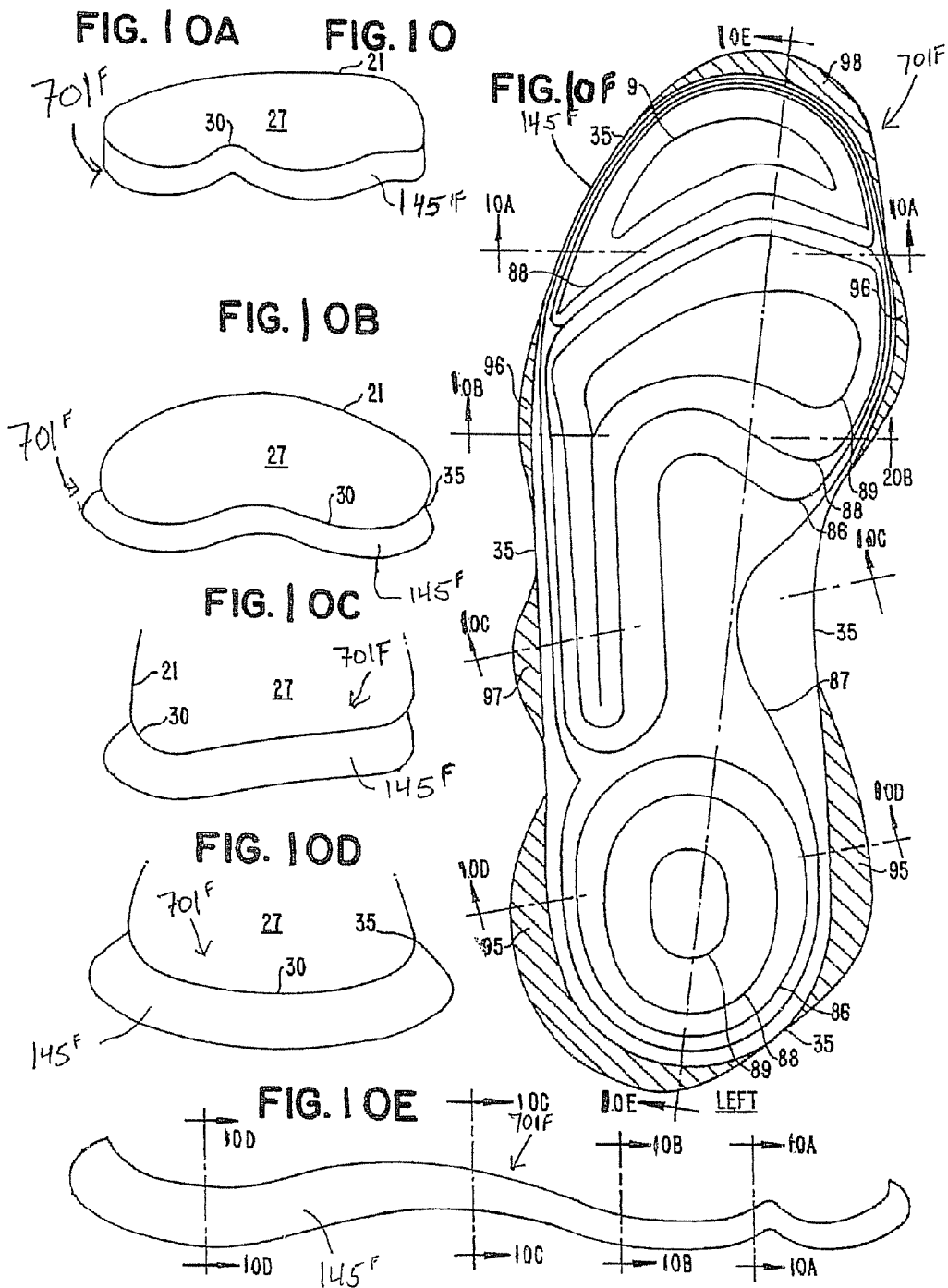

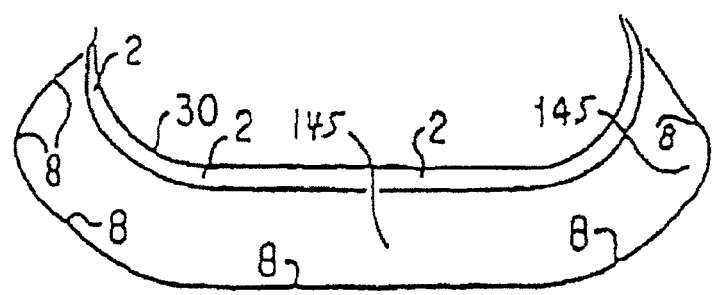
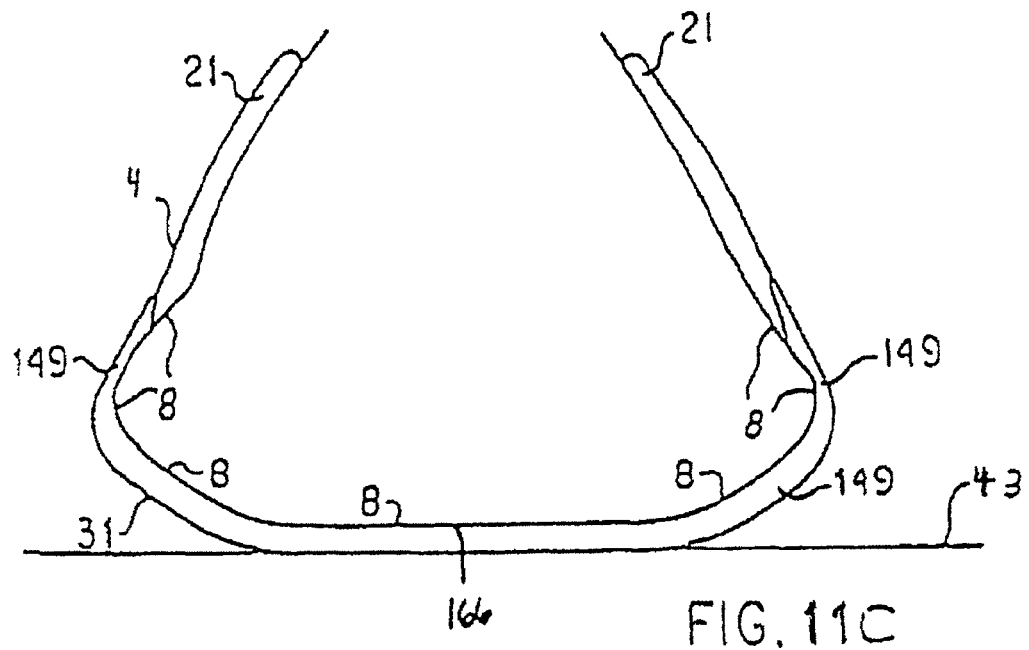

FIG. 11D
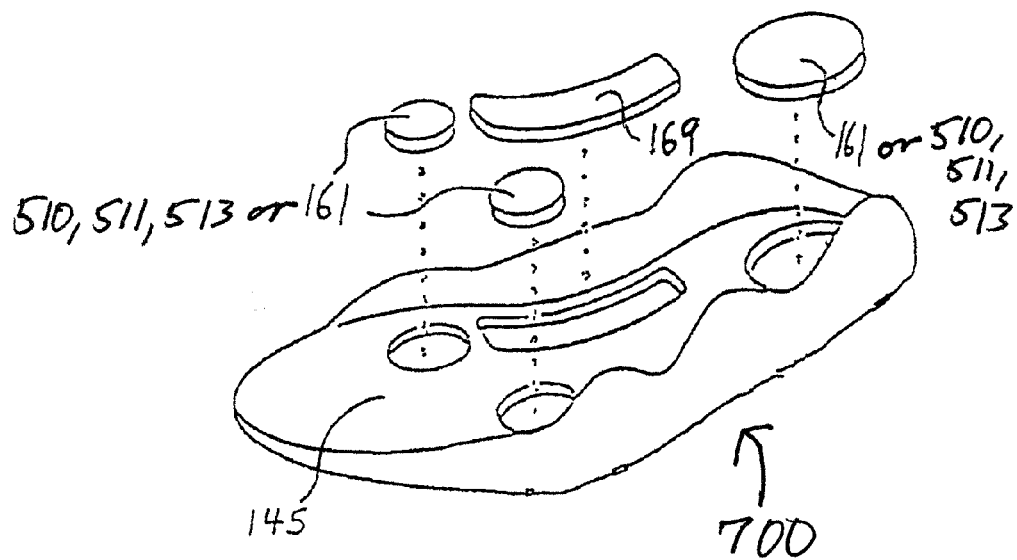
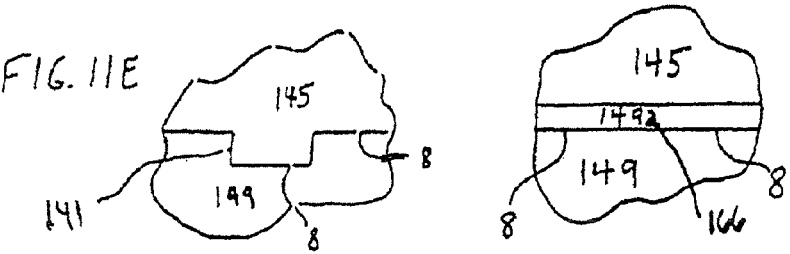
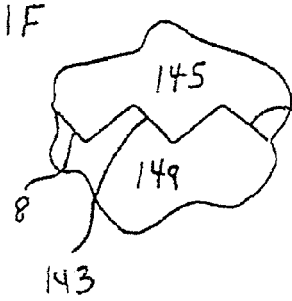
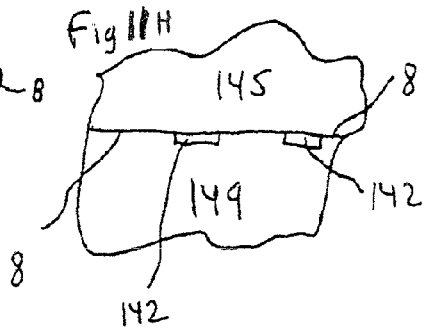

SETS OF ORTHOTIC OR OTHER FOOTWEAR INSERTS AND/OR SOLES WITH PROGRESSIVE CORRECTIONS

CROSS-REFERENCE TO RELATED APPLICATIONS

This application claims priority to provisional application No. 60/929,485 filed Jun. 29, 2007; provisional application No. 60/929,663 filed Jul. 6, 2007; provisional application No. 60/929,672 filed Jul. 9, 2007; and provisional application No. 60/935,555 filed Aug. 17, 2007.

BACKGROUND OF THE INVENTION

1. Field of the Invention

The present invention relates to sets of inserts, footwear soles and/or orthotics which employ a progression of corrective structures.

2. Brief Description of the Background of the Invention

Footwear soles and orthotics can be improved by using a progression of corrections in a series of soles or orthotics (or both) or inserts thereto that are used sequentially by a wearer. The progression of footwear sole and/or orthotic corrections can use, for example, incremental improvements in foot position (starting from an untreated, original state) by progressing through a series of incremental intermediate states, each controlled by the form of a sole or orthotic with a incremental improvement compared to the previous state, to a final or corrected state. Thus, a major correction can be achieved over time through a progressive series of relatively minor changes better tolerated by a wearer and to which the bones and other structures of the foot can more safely adapt.

SUMMARY OF THE INVENTION

In one aspect, the invention relates to a footwear sole or an orthotic or combinations of both including a set of incrementally different inserts forming a progressive sequence. The progressive sequence includes inserts having corrective structures that are incrementally closer to a final corrective structure than a corrective structure of a previous insert in the sequence. The corrective structure of the inserts may change in one or more of shape, thickness and firmness of at least one portion of the at least one insert as compared to the previous insert in the sequence. Each of the inserts of the set is worn for a period of time in order of the progressive sequence as part of the footwear sole and/or orthotic.

In a second aspect, the invention relates to a set of incrementally different footwear soles or orthotics or combinations of both forming a progressive sequence. The progressive sequence includes at least one sole and/or orthotic that comprises a corrective structure that is incrementally closer to a final corrective structure than at least one of a previous sole and orthotic in the sequence. The corrective structure of the at least one sole and/or orthotic is provided by at least a change in at least one of a shape, thickness and firmness of at least one portion of the at least one sole and/or orthotic as compared to the previous sole and/or orthotic in the sequence. Each of the inserts of the set is worn for a period of time in order of the progressive sequence as part of the footwear sole and/or orthotic.

In a third aspect, the present invention relates to a footwear sole or an orthotic or combinations of both, comprising a set of incrementally different inserts forming a progressive sequence. The progressive sequence includes at least one insert comprising a corrective structure that is incrementally closer to a final corrective structure than at least one previous insert in the sequence. The corrective structure of the at least one insert is provided by at least a change in shape of at least one portion of the at least one insert as compared to the previous insert in the sequence. Each of the inserts of the set is worn for a period of time in order of the progressive sequence as part of the footwear sole and/or orthotic.

Each intermediate and final state of the correction process can have a separate set (typically, for right and left feet) of progressively corrective footwear soles or orthotics (or combinations of both) or inserts therefor, and can be made using any of the many forms of mechanical drawing or electronic design, including graphical or computer aided design/computer aided manufacturing (CAD/CAM) techniques. The original or uncorrected state of a foot or feet to be corrected can be determined by any conventional or new molding or scanning processes (laser, MRI, CT, mechanical, or other) or other measuring technique in an unloaded condition or with any load, like full or partial body weight, for example, and can be for a specific individual in a custom set (either prescribed by a medical, podiatric, or other professional or not prescriptive) or a standard set for similar categories of individuals (such as standard size and typical foot form, like a pronated or supinated foot position), also potentially prescribed or not. A wearer can be human or animal. The use of the invention can involve, for example, a static condition in adulthood or a dynamic condition like a progressive disease or growth, or any combination thereof. Any organic or inorganic growth or corrective process can also incorporate the invention.

The incremental intermediate states of the progressively corrected footwear soles or orthotics or inserts therefore can be of any finite number, with three or five or 10 or 15 or 20 being useful examples. Each corrective state (beginning, intermediate corrective increments, and final correct correction) can have a separate set of footwear soles or orthotics (including uppers of either) or both, each with improvements progressively closer to a final corrected state. Each set of progressively corrected footwear soles or orthotics can be worn for a limited period of time, such as a week or month, for example, while the final, corrected set can be used permanently, either full time or intermittently, like dental retainers, to maintain the corrected state. Monitoring and/or testing and/or new scanning of the wearer and the wearer's foot or feet can be done at any time while the progressively corrective footwear soles and/or orthotics are in use, and adjustment or replacement of the progressively corrected footwear soles and/or orthotics can occur as necessary. In general, the invention uses progressive or incremental corrections in a manner that is in some ways similar to Invisalign™ Orthodontic Appliances (a new form of braces known in the dental art).

Since walking and running involve different biomechanics, particularly during the support phase, the progressively corrective footwear soles and/or orthotics can be designed specifically for either form of locomotion (or for other forms of locomotion or exercise or sport, including those involving greater degrees of lateral motion).

The progressively corrected footwear sole or orthotic or inserts therefor can be or include an insole and/or midsole and/or midsole component, including a compartment or chamber or bladder (like for example Nike Air™) and/or outer sole (or bottom sole) and can include part or all of an upper, and the entire footwear or orthotic can be formed from one material suitable for soles (like Crocs™ or Waldies™ clog-like commercial examples) or from more than one material like a common modern athletic shoe well known in the prior art.

The progressively corrected footwear soles or orthotics or both can be a part or all of an otherwise conventional footwear sole or orthotic, or can be a removable midsole insert or removeable orthotic insert, although the applicant's previous footwear inventions based on the barefoot and described in previous patents and patent applications (from the '665 application incorporated herein later in this application) are preferred, including the applicant's removeable midsole insert or removable orthotic insert 145.

BRIEF DESCRIPTION OF THE DRAWINGS

FIG. 9 shows multiple parallel plane cross section views of an initial or original orthotic insert $145^0$ and a final orthotic insert $145^F$ (or removable midsole insert $145^0$ or $145^F$). The upper 21 and bottom sole 149 can be integrated to form one piece such as is done in Classic Crocs™ or Waldies™.

FIG. 10 shows multiple parallel plane cross section views of an initial or original orthotic insert $145^0$ and a final orthotic insert $145^F$ (or removable midsole insert $145^0$ or $145^F$). The orthotic insert 145F can include a bottom sole 149 and upper 21, as in the embodiments of FIG. 9, though not shown in this FIG. 10. The embodiment of FIG. 10E includes a heel lift 38 though the heel lift 38 is not separately shown in FIG. 10E.

FIGS. 11B-H show other views from the '665 application including an example of the incremental correction 700 invention with the insert 145 and the applicant's 510 or 511 or 513 inventions. FIGS. 11B-11C also show frontal plane cross sections of the invention in an upright, unloaded condition.

DETAILED DESCRIPTION OF THE PREFERRED EMBODIMENTS

"Corrective structure" and "correction" are used interchangeably in this patent application with reference to an insert, footwear sole, orthotic, or portion thereof, to refer to the structure of the insert, footwear sole, orthotic, or portion thereof designed to provide a correction to an intended wearer.

Figure 1:
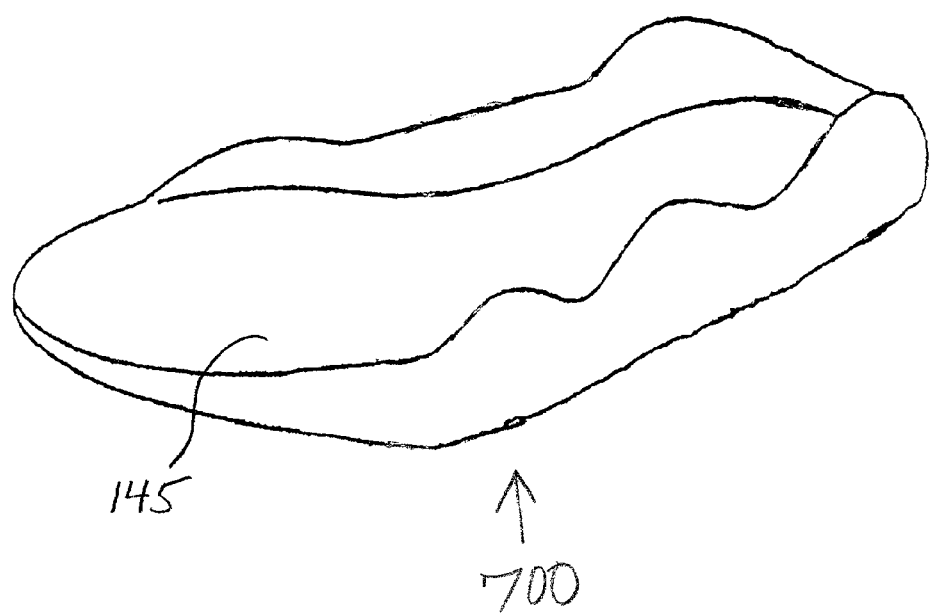
FIG. 1 is a perspective view of a footwear sole 22 or 28 or removeable midsole or orthotic insert 145 for a progressively corrected footwear sole or orthotic 700.

As an example embodiment, FIG. 1 shows a perspective view of the progressively corrected footwear sole or orthotic 700 in the specific form of a removable midsole or orthotic insert 145, which can be either a part or all of a footwear sole 28 or 22 or of an orthotic sole, and can include or incorporate all or part of a footwear or orthotic upper 21. The insert 145 is insertable into the footwear sole or orthotic by a wearer in the same manner in which a wearer conventionally inserts a foot into the footwear or orthotic.

Figure 2:
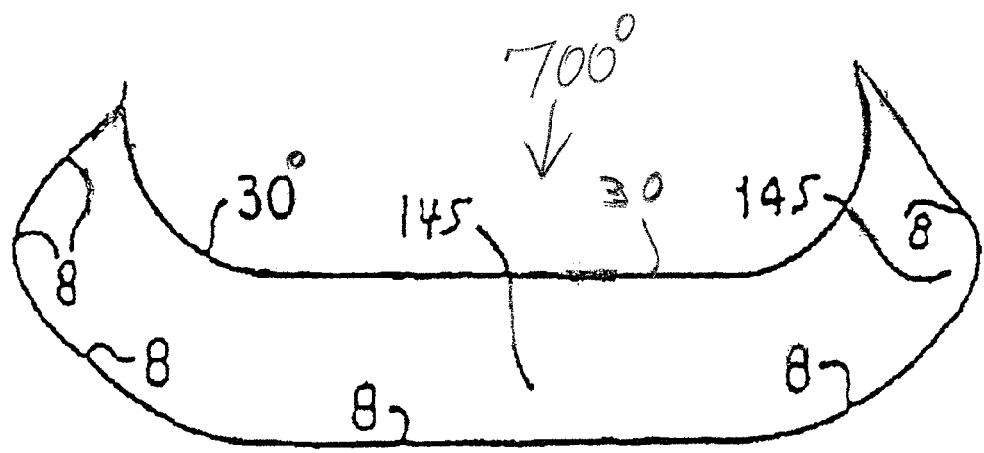
FIGS. 2-5 show an insert 145 with incrementally increasing inner or upper surfaces 30 for a progressively corrected footwear sole or orthotic 700, as viewed in a frontal plane cross section in an upright, unloaded condition.

FIG. 2 shows of the removable midsole or orthotic insert 145 in an unloaded, upright frontal plane cross section, like FIG. 11B (without insole 2) of the applicant' U.S. application Ser. No. 11/282,665 filed Nov. 21, 2005, and published on Nov. 9, 2006, as Publication No. US 2006/0248749 A1, which is incorporated by reference herein in its entirety. FIG. 2 shows an original or starting inner or upper surface $30^0$ for a progressively corrected footwear sole or orthotic 700, shown as $700^0$.

Figure 3:
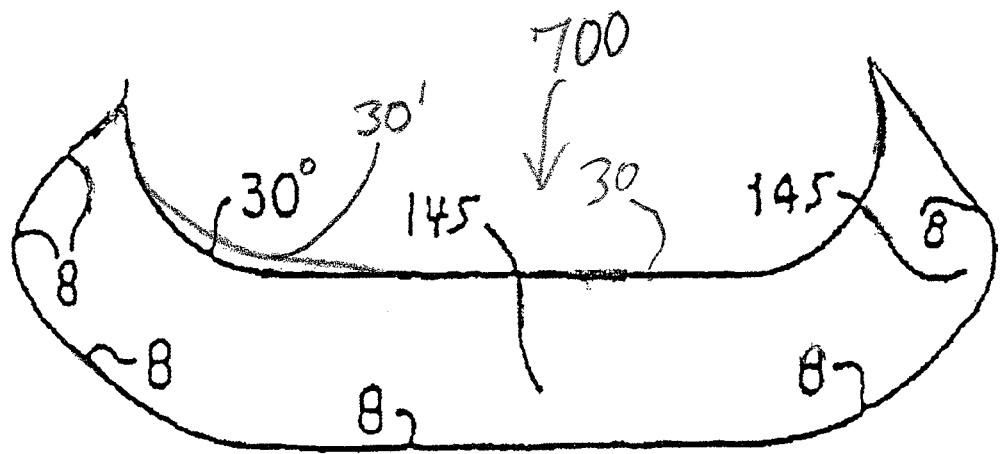
Figure 6:
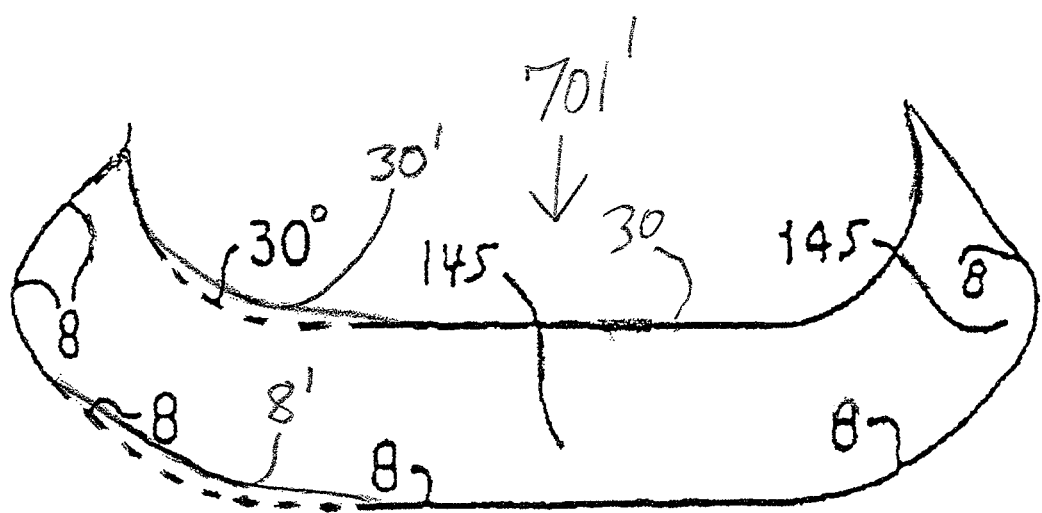
FIGS. 6-8 show an insert 145 with incrementally increasing inner or upper surfaces 30 and a lower surface 8 incrementally decreasing in parallel for a progressively corrected footwear sole or orthotic 700, as viewed in a frontal plane cross section in an upright, unloaded condition.
Figure 7:
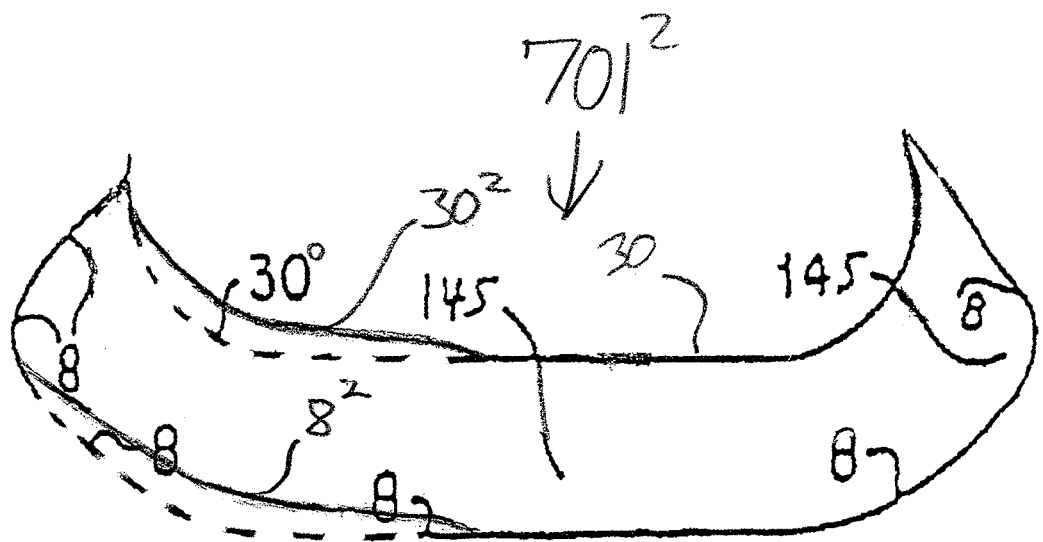
Figure 8:
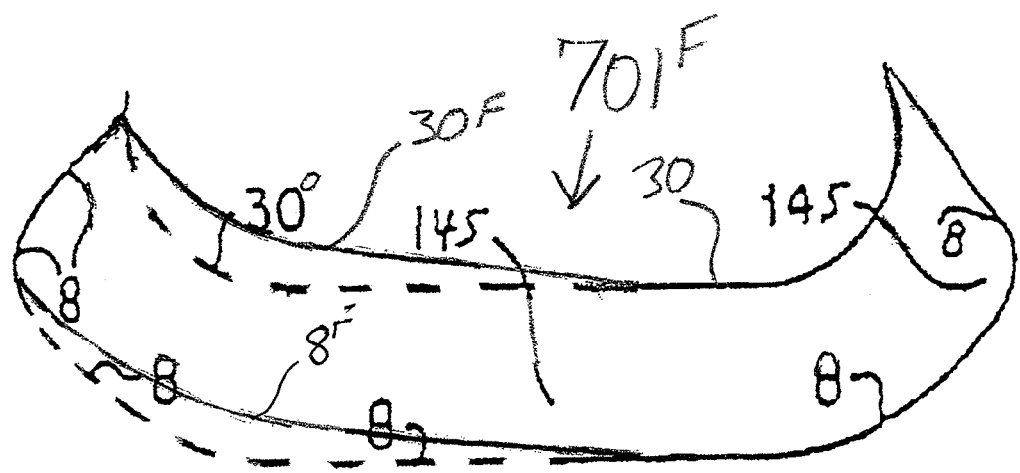

FIG. 3 shows the same figure as FIG. 2, but with an example of a new incremental corrective inner surface $30^1$, the progressively corrected footwear sole or orthotic 700, shown as $700^1$, therefore being thicker in the area of inner surface $30^1$. Alternatively, the incremental correction or corrective structure shown in inner surface $30^1$ could instead be made in outer surface 8 (as could subsequent corrections in FIGS. 4 and 5), as shown in FIGS. 6-8. Also, material density or firmness increases (like those shown in FIGS. 21-23 and 25 of the incorporated '665 application) in the sole or orthotic area adjacent to inner surface $30^1$ can produce a similar corrective effect. Decreases in thickness or material density or firmness (like those shown in FIGS. 27A-C, 28C-D and 28F of the incorporated '665 application) in the sole or orthotic can also be used for a corrective effect. Such progressive corrections can be made anywhere in or on the footwear sole or orthotic (or upper of either) or in combinations of both, including variations in frontal plane cross sections in different parts of the sole, such as the forefoot, heel, or midfoot portions (as shown in FIGS. 28A-F of the incorporated '665 application).

Figure 4:
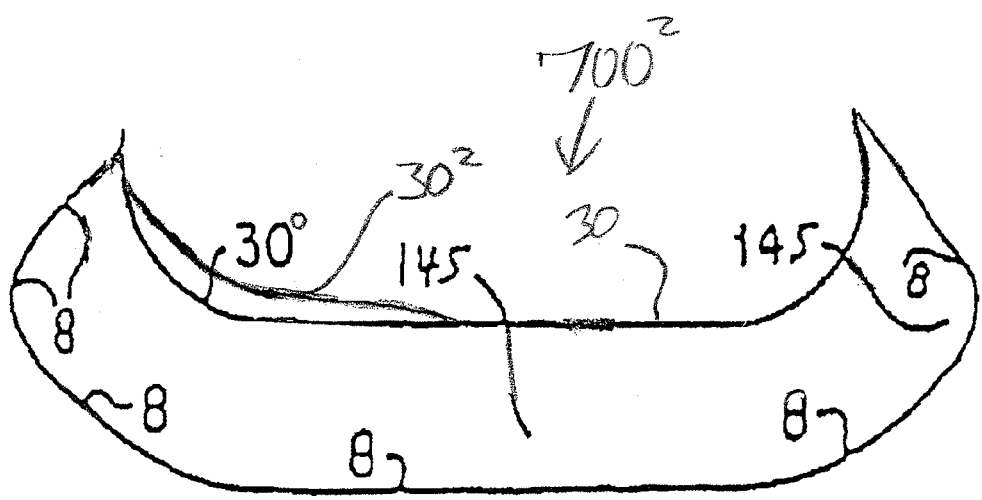

FIG. 4 shows the same figure as FIG. 3, but with another progressive example of an even thicker new incremental corrective inner surface $30^2$ for a progressively corrected footwear sole or orthotic 700, shown as $700^2$. Other thickness or material firmness or density correction increments are possible, as previously described in FIG. 3 above.

Figure 5:
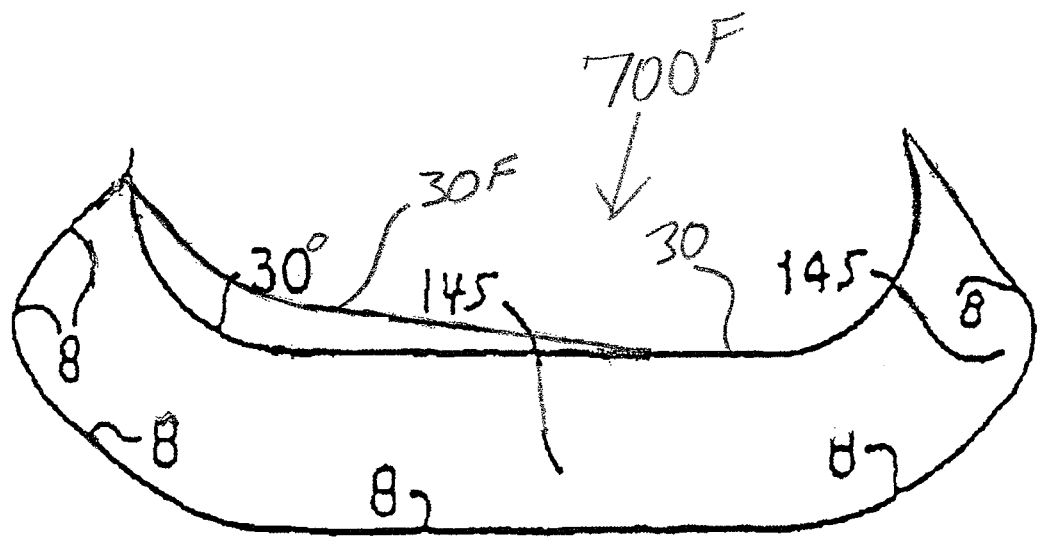

FIG. 5 shows the same figure as FIGS. 2-4, but with another progressive example of an even thicker final new incremental corrective inner surface $30^F$, for a progressively corrected footwear sole or orthotic 700, shown as $700^F$ Again, other thickness or material firmness or density correction increments are possible, as previously described in FIGS. 3 and 4 above.

Although corrections in the form of thickness increases caused by changes in the inner surface 30 of the example removable midsole or orthotic insert 145 are shown above in FIGS. 3-5, similar corrections can be made in the outer surface 31 (shown in FIG. 11C and other figures of the incorporated '665 application) of the footwear sole or orthotic, including the bottom or sides. Such outer surface 31 corrections can be made independently or in combination with the inner surface 30 corrections described in FIGS. 3-5 above (and are shown combined in FIGS. 6-8 below). Other thickness or material firmness or density corrections can be used in outer surface 31 corrections, as previously described for inner surface 30 corrections in FIG. 3 above.

In summary, this embodiment of the invention includes a footwear sole or an orthotic or combinations of both including a set of incrementally different inserts forming a progressive sequence. The progressive sequence includes inserts having corrective structures that are incrementally closer to a final corrective structure than a corrective structure of a previous insert in the sequence. The corrective structure of the inserts may change in one or more of shape, thickness and firmness of at least one portion of the at least one insert as compared to the previous insert in the sequence. Each of the inserts of the set is worn for a period of time in order of the progressive sequence as part of the footwear sole and/or orthotic.

FIGS. 6-8 show the same figures as FIGS. 3-5, but with the outer surface 8 of the removable midsole or orthotic insert 145 shown modified in parallel (including curves) with the inner surface 30 corrections of FIGS. 3-5, so that the thickness of the progressively corrected footwear sole or orthotic 701, remains substantially the same (although the figures shown are somewhat approximate), while the shape only of the insert 145 is modified incrementally and progressively from FIG. 6 through FIG. 8, shown as $701^1$, $701^2$, and $701^F$, with outer surface 8 of the insert 145 changing from $8^0$ to $8^1$, then $8^2$, and finally $8^F$.

In summary, this embodiment of the invention includes a footwear sole or an orthotic or combinations of both, comprising a set of incrementally different inserts forming a progressive sequence. The progressive sequence includes at least one insert comprising a corrective structure that is incrementally closer to a final corrective structure than at least one previous insert in the sequence. The corrective structure of the at least one insert is provided by at least a change in shape of at least one portion of the at least one insert as compared to the previous insert in the sequence. Each of the inserts of the set is worn for a period of time in order of the progressive sequence as part of the footwear sole and/or orthotic.

FIGS. 9A-F show (in multiple frontal A-D, longitudinal E, and horizontal F plane cross sections) an example of the invention $701^O$ in the form of a removable midsole or orthotic insert $145^O$ (composed of midsole material 148, for example) with inner and outer surfaces that conform to the shape of a wearer's load-bearing foot sole (with both curved portions, for example under the wearer's main longitudinal arch, and flatten portions, for example under the wearer's heel). The outer or bottom sole 149 is shown with all of the middle portion flattened so that some portions are flattened where some portions of the adjacent insert 145 are curved; this is an example of an economically lower cost approach to incorporating a set of one or more incrementally different inserts 145 that are customized for the individual user that can be used with a non-customized, standard sized bottom sole and upper. Also, FIG. 9 shows an upper 21 that is integrated into the bottom sole 149 (and/or midsole 148) so that the bottom sole and upper can be made of the same material, such as a foamed plastic like classic Crocs™ or Waldies™ clogs.

In addition, FIGS. 9A-F show an example of an initial state or original removable midsole or orthotic insert $145^O$, while corresponding FIGS. 10A-F show an example of a final state of a removable midsole or orthotic insert $145^F$ wherein the corrected insert is fully rounded like a wearer's unloaded foot sole in a neutral, upright position. FIGS. 10A-F can include a bottom sole 149 and upper 21, as well as a heel lift, like FIGS. 9A-F (not shown separately).

Figure 11A:
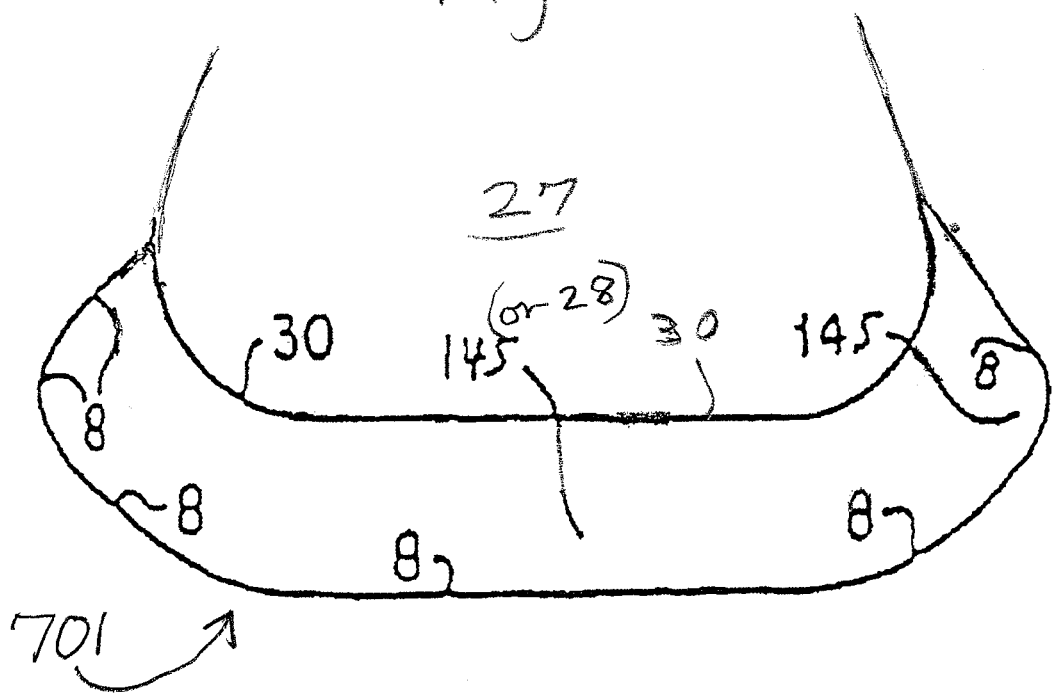
FIG. 11A shows a sole or orthotic insert 145 with a thermal-pressure moldable material, as viewed in a frontal plane cross section with the shoe or orthotic insert 145 in an upright, unloaded condition.

FIG. 11A shows an example of the invention 701 as a sole 28 or insert 145 with an inner sole layer (and/or insole) including a combined pressure and thermally moldable material such that a wearer can at least partially or fully custom mold the inner surface 30 to the shape of the wearer's foot sole 27, in a manner similar to a Montrail™ CTX™ foam material used in a Molokai or Molokini model sandal.

FIGS. 11B-H are from the applicant's previously incorporated prior '665 application showing examples of the removable midsole or orthotic insert 145 in various FIG. 11B-11H embodiments, including a FIG. 11D perspective view of the incremental correction 700 invention with an insert 145 example with compartments 161 or the 510 or 511 or 513 invention. FIGS. 11G and 11H are FIGS. 11S and 11V of the incorporated '665 application.

Figure 12:
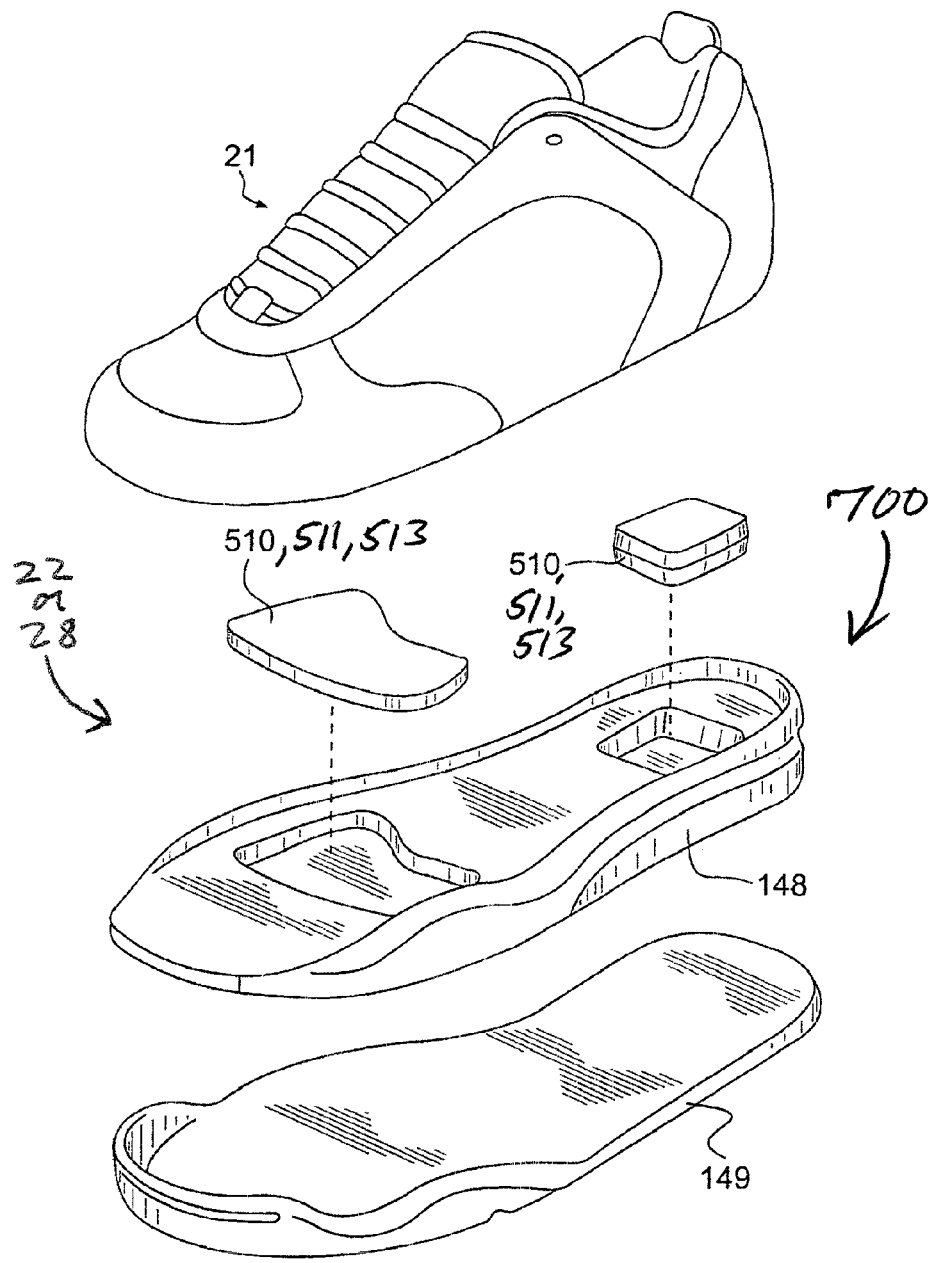
FIG. 12 shows FIG. 1C from the application Ser. No. 11/802,930 with an example of the incremental correction 700 invention and the applicant's 510 or 511 or 513 inventions.

FIG. 12 is FIG. 1C from the applicant's incorporated prior application Ser. No. 11/802,930 and shows the incremental correction 700 invention in a footwear sole 22 or 28 or orthotic with one or more of the applicant's 510 or 511 or 513 invention.

The above described examples can provide a typical excessively pronated foot (i.e. often called a "flat foot") with progressive correction to a more normal position with better defined longitudinal arches results in a corrected footwear sole or orthotic that better supports the foot's natural function by maintaining its natural shape, while deforming under body weight pressure as does the wearer's bare foot, providing a more natural energy return with each stride during locomotion.

Many of the typical foot problems known to podiatrics and/or orthopedics can be advantageously treated using the above described approaches employing progressively corrected sets of footwear soles and/or orthotics 700 or 701. To take but one simple example, a hammer toe deformity, either on a single foot or bilaterally, can be corrected in the manner described above, in which the normal arches (longitudinal and transverse) of the foot or feet are restored through gradual correction, during which process the position of the big toe is straightened from a bent in position to a more normal, straighter position.

Generally, the progressively corrected sets of footwear soles and/or orthotics 700 or 701 provide a way of correcting bilateral skeletal asymmetry in bipedal humans (and animals, including non-bipedal), including both right versus left foot and ankle asymmetry, but also all other bilateral asymmetries, including of the lower limbs and associated knee and hip joints, as well as the pelvis and lumbar spinal, and the rest of the spine, including the cervical spine, and all other associated upper body limbs and joints, including the skull, and associated muscles, ligaments, and tendons, and soft tissues, such as the viscera contained and supported by the pelvis, for example. The gradual correction provided by the progressively corrected soles or orthotics 700 or 701 allow for gradual bone reformation where the outset of gradual pain can be a guide to modifying or further slowing the correction, whereas imposing the entire correction at once is likely to result in significant pain and/or sudden joint injury of potentially serious nature, especially if the initial diagnosis or correction parameters prove to be incorrect and therefore in need of modification.

The gradual correction of the soles or orthotics 700 or 701 can include gradual modification of the amount of heel lift, such as gradual reduction, or gradual introduction of negative heel lift (i.e. forefoot lift). Similarly, any other footwear sole or orthotic corrections commonly used in orthopedics, podiatry, and related fields, including for example lateral wedges or posts, can be incrementally introduced.

Any example of a new invention of progressively corrected footwear soles and/or orthotics 700 or 701 shown in this application in the preceding FIGS. 1-11 and/or associated textual specification can be combined with any other part of any one or more other of the prior art or the applicant's prior invention examples shown in FIGS. 1-3, 5-7, 9, 11-42, 44-52, 55-62, 64-82 from prior published FIGS. 1-82 of the applicant's published application Ser. No. 11/282,665 previously incorporated by reference herein in its entirety, to make new and useful improvements over the existing art.

Such useful combinations include, but are not limited to, those combinations that include one or more features of FIGS. 1-11 and: incorporate uppers that envelope the midsole and/or outsole and/or other features shown in published application '665 prior FIGS. 5-7 and 13; incorporate anthropomorphic shapes and/or chambers and/or other features shown in prior FIGS. 9 and 10; incorporate integral or insertable orthotics or microprocessor-controlled variable pressure and/or other features shown in prior FIG. 11; incorporate sipes and/or other features shown in prior FIG. 12; use uniform thickness (measured in frontal plane cross-sections) in rounded sole side or sole bottom portions, especially at essential support and stability elements and/or other features shown in prior FIGS. 14-16, 29-46 and 76-77; use increased or decreased (or variable) thickness in rounded sole side portions and/or other features shown in prior FIGS. 17-20, 24, and 27-28; use increased or decreased density or firmness in rounded sole side or bottom portions and/or other features shown in prior FIGS. 21-23 and 25-26; use rounding of the outer surface of the midsole on a sole side and/or other features shown in prior FIG. 43A; employ bent-in rounded sides and/or other features shown in prior FIG. 47; uses bulges with or without uniform thickness, at important support or propulsion areas and/or features shown in prior FIGS. 48 and 75; incorporates a flat heel (meaning no heel lift) and/or other features shown in prior FIGS. 51A-51E; incorporates negative heel embodiments and/or other features shown in prior FIGS. 49A-49D and 50A-50E; use rounded sides with variable thickness and firmness and/or other features shown in prior FIG. 52; employs sipes and/or other features shown in prior FIGS. 53-57, 70-71 and 73; incorporates fiber and/or multiple layers of chambers and/or other features shown in prior FIGS. 58-60; employ shoe soles or orthotics with sufficient width throughout or at specific portions to support a wearer's bone structures throughout a full range of motion and/or other features shown in prior FIGS. 61-65 and 72; uses relatively planar sides with rounded underfoot sole portions and/or other features shown in prior FIGS. 66 and 67; uses similarly shaped rounding on sole sides of different thickness at different parts of the sole and/or other features shown in prior FIG. 69; uses a variation of heel or forefoot lifts and/or other features shown in FIG. 74; and/or other features shown in prior FIGS. 78-82.

In addition, any example of a new invention of progressively corrected footwear soles and/or orthotics 700 or 701 shown in this application in the preceding FIGS. 1-11 and/or associated textual specification can be combined with any other part of any one or more other of the prior art or the applicant's prior invention examples shown in prior published FIGS. 83-127 of the applicant's published application Ser. No. 11/282,665 previously incorporated by reference herein in its entirety, especially including the applicant's 510 or 511 or 513 inventions shown in FIGS. 83-114 of the '665 application, to make new and useful improvements over the existing art.

Such useful combinations include, but are not limited to, those combinations that include one or more features of FIGS. 1-11 and incorporate: one or more siped compartments, chambers, or bladders inserts 510 as shown generally in FIGS. 83-88, and in specific footwear or orthotic examples in FIGS. 89-96, including with computer-control in FIG. 97 and magnetic fluid in FIGS. 98-99; inserts 511 including also sipes shown generally in FIG. 100; unitary sipe or slit inserts 513 shown generally in FIG. 101-103; inserts 510 included in footwear uppers in FIGS. 104 and 105; inserts 510 and 513 in helmet examples in FIG. 106; inserts 510 incorporating midsole foamed materials in examples in FIGS. 107 and 108; insert 510 in a footwear sole or orthotic shank example; insert 510 in a ball example in FIG. 109, a tire example in FIG. 110, a human breast implant example in FIG. 111, a structural or support element in FIG. 112, a golf club example in FIG. 113, and a spinal disk example in FIG. 114, as well as many other examples described in paragraphs 0534, 0535, and 0536.

Furthermore, any example of a new invention of progressively corrected footwear soles and/or orthotics 700 or 701 shown in this application in the preceding FIGS. 1-11, and/or associated textual specification can be combined with any other part of any one or more other of the prior art or the applicant's prior invention examples shown in FIGS. 1-87 of the applicant's U.S. patent application Ser. No. 11/802,033, published on Apr. 10, 2008 as Pub. No. 2008/0083140 A1 which is incorporated by reference herein in its entirety, especially including the applicant's 510 or 511 or 513 inventions shown in FIGS. 45-87 of the '930 application, to make new and useful improvements over the existing art.

In addition, any example of a new invention of progressively corrected footwear soles and/or orthotics 700 or 701 shown in this application in the preceding FIGS. 1-11, and/or associated textual specification can be combined with any other part of any one or more other of the prior art or the applicant's prior invention examples shown in FIGS. 1-87 of the applicant's patent application Ser. No. 11/802,930, published on Apr. 17, 2008 as Pub. No. US 2008/0086916 A1, which is incorporated by reference herein in its entirety, especially including the applicant's 510 or 511 or 513 inventions shown in FIGS. 45-87 of the '930 application, to make new and useful improvements over the existing art.

The applicant's other footwear U.S. Pat. Nos. 4,989,349; 5,317,819; 5,544,429; 5,909,948; 6,115,941; 6,115,945; 6,163,982; 6,308,439; 6,314,662; 6,295,744; 6,360,453; 6,487,795; 6,584,706; 6,591,519; 6,609,312; 6,629,376; 6,662,470; 6,675,498; 6,675,499; 6,708,424; 6,729,046; 6,748,674; 6,763,616; 6,789,331; 6,810,606; 6,877,254; 6,918,197; 7,010,869; 7,082,697; 7,093,379; 7,127,834; 7,168,185; 7,174,658; 7,234,249; 7,287,341; 7,334,350; and 7,334,356 are hereby incorporated by reference herein in their entirety into this application for completeness of disclosure of the applicant's novel and useful combination of one or more of any of the features or components of any of the figures of this application with one or more of any of the features of any one or more of the preceding applicant's patents listed above in this paragraph to make new and useful improvements over the existing art.

The applicant's other footwear published U.S. Application Numbers 20020000051; 20020007571; 20020007572; 20020014020; 20020014021; 20020023373; 20020073578; 20020116841; 20030046830; 20030070320; 20030079375; 20030131497; 20030208926; 20030217482; 20040134096; 20040250447; 20050016020; 20050086837; 20050217143; 20060032086; 20060248749; 20070240332; 20070271817; 20080000108; 20080005931; and 20080022556 are hereby incorporated by reference herein in their entirety into this application for completeness of disclosure of the applicant's novel and useful combination of one or more of any of the features or components of any of the figures of this application with one or more of any of the features of any one or more of the preceding applicant's published U.S. Applications listed above in this paragraph to make new and useful improvements over the existing art.

The invention claimed is:
1. Orthotics or other footwear inserts for an intended wearer, comprising:
    a set of separate and incrementally different inserts sized and adapted for a right and/or left foot of the intended wearer;

one said insert in said set having a first corrective structure and at least another said insert in said set having a second corrective structure that is at least incrementally different from the first corrective structure; as viewed in a frontal plane cross section taken at a same location of each of said inserts in said set, when said inserts in said set are upright and in an unloaded condition;

the second corrective structure including at least an incremental change in one or more of curvature, thickness and firmness of at least one sidemost portion of said insert in said set as compared to the first corrective structure and a corrective structure of each other said insert in said set, when viewed in a frontal plane cross-section when said orthotics or other footwear inserts are upright and in an unloaded condition;

the at least one sidemost portion is located proximate to one or more of a first distal phalange, a head of a first metatarsal, a head of a fifth metatarsal, a base of a fifth metatarsal and a lateral tuberosity of a calcaneus of the intended wearer's foot when located in footwear including said orthotics or other footwear inserts;

inner and outer surfaces of said sidemost portion being curved concavely to define a concavely curved sidemost portion, as determined relative to a central portion of an intended wearer's foot location in the footwear including said orthotics or other footwear inserts, as viewed in a frontal plane cross-section when the footwear including said orthotics or other footwear inserts is upright and in an unloaded condition;

said inserts in said set having a progressive sequence based on an increase or decrease in one of the curvature, thickness and firmness of said at least one sidemost portion of each said insert in said set; and wherein said orthotics or other footwear inserts comprising each said insert in said set are adapted to be worn one at a time for a period of time using said inserts in said set sequentially based on the progressive sequence.

2. The orthotics or other footwear inserts of claim 1, wherein said set of inserts includes at least three said separate inserts arranged in the progressive sequence.

3. The orthotics or other footwear inserts of claim 2, including at least one said insert of said set that comprises one said corrective structure that is incrementally closer in one of curvature, thickness and firmness to the second corrective structure than the first corrective structure.

4. The orthotics or other footwear inserts of claim 2, wherein each of said inserts of said set except said insert of said set comprising the first corrected structure comprises one said corrective structure that is at least incrementally closer in one of curvature, thickness and firmness to the second corrective structure than the first corrective structure.

5. The orthotics or other footwear inserts of claim 1, wherein said set of inserts includes at least four said separate inserts arranged in the progressive sequence.

6. The orthotics or other footwear inserts of claim 5, wherein said set of inserts comprises one subset of said inserts of said set for a right foot and one subset of said inserts of said set for a left foot.

7. The orthotics or other footwear inserts of claim 5, wherein said set of inserts is custom fit to an individual wearer's foot sole.

8. At least one shoe comprising the orthotics or other footwear inserts of claim 7, wherein each said at least one shoe comprises an outer sole and an upper, and wherein the outer sole and upper of each said at least one shoe is sized using standard shoe sizes.

9. The orthotics or other footwear inserts of claim 7, wherein at least one of said set of inserts includes a sole layer defining an inner surface of said at least one insert of said set, said sole layer comprising a material that is moldable to a desired shape by a combination of application of pressure and heat such that an individual wearer can mold at least a part of the inner surface of at least one said insert of said set to the shape of the wearer's foot sole.

10. The orthotics or other footwear inserts of claim 7, wherein each of said inserts of said set is insertable into an outer sole by an intended wearer.

11. The orthotics or other footwear inserts of claim 1, wherein said set of inserts includes at least eight said separate inserts arranged in the progressive sequence.

12. The set of orthotics or other footwear inserts as claimed in claim 1, wherein said second corrective structure comprises at least a change in curvature of the at least one sidemost portion of said at least one insert of said set as compared to said first corrective structure of at least one other said insert of said set.

13. The orthotics or other footwear inserts of claim 12, wherein at least one said insert of said set has an inner surface and an outer surface that are parallel to each other between a position proximate to a lateral sidemost extent and a position proximate to a medial sidemost extent, as viewed in at least one frontal plane cross section when said at least one insert of said set is upright and in an unloaded condition.

14. The orthotics or other footwear inserts of claim 13, wherein the inner surface and the outer surface of at least two said inserts of said set are parallel to each other between a position proximate to a lateral sidemost extent and a position proximate to a medial sidemost extent as viewed in at least one frontal plane cross section when said at least two inserts of said set are upright and in an unloaded condition.

15. The orthotics or other footwear inserts of claim 12, wherein said at least one insert of said set has a uniform radial thickness between an inner surface and an outer surface, the uniform radial thickness extending from a position proximate to a lateral sidemost extent of said at least one insert of said set to a position proximate to a medial sidemost extent of said at least one insert of said set, as measured in a frontal plane cross section when said at least one insert of said set is upright and in an unloaded condition; and the uniform radial thickness being different in at least two different frontal plane cross sections of said at least one insert of said set.

16. The orthotics or other footwear inserts of claim 12, wherein an inner surface and an outer surface of at least two said inserts of said set are substantially parallel to each other between a position proximate to a lateral sidemost extent and a position proximate to a medial sidemost extent, as viewed in at least one frontal plane cross section when said at least two inserts of said set are upright and in an unloaded condition.

17. The orthotics or other footwear inserts of claim 16, wherein the inner surface and the outer surface of each of said at least two inserts of said set are parallel in a second portion of said at least two inserts of said with the change in curvature of the corrective structure, as viewed in at least one frontal plane cross section when said at least two inserts of said set are upright and in an unloaded condition.

18. The orthotics or other footwear inserts of claim 12, wherein each said insert of said set except said insert of said set having said first corrective structure comprises one said corrective structure that is at least incrementally closer in curvature to the second corrective structure than the first corrective structure.

19. A set of separate and incrementally different footwear soles sized and adapted for a right and/or left foot of the intended wearer;
- one said footwear sole of said set comprising a first corrective structure and at least one other said footwear sole of said set comprising a second corrective structure that is at least incrementally different from the first corrective structure, as viewed in a frontal plane cross section taken at a same location of each of said footwear soles in said set when said footwear sole of said set is upright and in an unloaded condition;
- the second corrective structure including at least an incremental change in one or more of curvature, thickness and firmness of at least one side portion of each said footwear sole of said set as compared to the first corrective structure and a corrective structure of each other said footwear sole of said set, when viewed in a frontal plane cross-section when said footwear inserts are upright and in an unloaded condition;
- the at least one sidemost portion is located proximate to one or more of a first distal phalange, a head of a first metatarsal, a head of a fifth metatarsal, a base of a fifth metatarsal and a lateral tuberosity of a calcaneus of the intended wearer's foot when located in footwear including said footwear soles;
- inner and outer surfaces of said sidemost portion being curved concavely to define a concavely curved sidemost portion, as determined relative to a central portion of an intended wearer's foot location in the footwear including said footwear soles, as viewed in a frontal plane cross-section when the footwear including said footwear soles is upright and in an unloaded condition;
- said footwear soles in said set having a progressive sequence based on an increase or decrease in one of the curvature and thickness of said at least one sidemost portion of each said footwear sole in said set; and
- wherein said footwear soles of said set are adapted to be worn one at a time for a period of time using said footwear soles in said set sequentially based on the progressive sequence.

20. The footwear soles of claim 19, wherein said set of footwear soles includes at least three said separate footwear soles of said set arranged in the progressive sequence.

21. The footwear soles of claim 19, wherein said set of footwear soles includes at least four said separate footwear soles of said set arranged in the progressive sequence.

22. The footwear soles of claim 21, wherein one said corrective structure of at least one said footwear sole of said set includes at least a change in curvature.

23. The footwear soles of claim 21, wherein said set of footwear soles comprises a subset of said footwear soles of said set for a right foot and a subset of said footwear soles of said set for a left foot.

24. The footwear soles of claim 21, wherein said set of footwear soles is custom fit to an individual wearer's foot sole.

25. The footwear soles of claim 19, wherein said set of footwear soles includes at least eight said separate footwear soles of said set arranged in the progressive sequence.

26. The footwear soles of claim 19, wherein an inner surface and an outer surface of at least two said footwear soles of said set are substantially parallel to each other between a position proximate to a lateral sidemost extent and a position proximate to a medial sidemost extent, as viewed in at least one frontal plane cross section when said at least two footwear soles of said set are upright and in an unloaded condition.

27. A set of integrated shoe soles and orthotics, each of said integrated shoe soles and orthotics comprising:
- a shoe sole, and
- an orthotic,
- said integrated shoe soles and orthotics include at least one common material,
- one said integrated shoe sole and orthotic having a first corrective structure and at least one said integrated shoe sole and orthotic having a corrective structure that is at least incrementally different from the first corrective structure, as viewed in a frontal plane cross section taken at a same location of each said integrated shoe sole and orthotic when said integrated shoe sole and orthotic is upright and in an unloaded condition;
- each said corrective structure that is at least incrementally different from the first corrective structure including at least a change in one or more of curvature, thickness and firmness of at least one sidemost portion of said integrated shoe sole and orthotic as compared to the first corrective structure and the corrective structure of each other said integrated shoe sole and orthotic when viewed in a frontal plane cross-section when said integrated shoe soles and orthotics are upright and in an unloaded condition;
- the at least one sidemost portion is located proximate to one or more of a first distal phalange, a head of a first metatarsal, a head of a fifth metatarsal, a base of a fifth metatarsal and a lateral tuberosity of a calcaneus of the intended wearer's foot when located in footwear including said integrated shoe soles and orthotics;
- inner and outer surfaces of said sidemost portion being curved concavely to define a concavely curved sidemost portion, as determined relative to a central portion of an intended wearer's foot location in the footwear including said integrated shoe soles and orthotics, as viewed in a frontal plane cross-section when the footwear including said integrated shoe soles and orthotics is upright and in an unloaded condition;
- said set of integrated shoe soles and orthotics having a progressive sequence based on an increase or decrease in one of the curvature, thickness and firmness of said at least one sidemost portion of each said integrated shoe sole and orthotic; and
- wherein each said integrated shoe sole and orthotic is adapted to be worn one at a time for a period of time sequentially based on the progressive sequence.

28. The set of integrated shoe soles and orthotics as claimed in claim 27, wherein said integrated shoe soles and orthotics further comprise an upper including at least the same common material.

29. The set of integrated shoe soles and orthotics as claimed in claim 27, wherein said integrated shoe soles and orthotics are principally formed from one material.

30. The set of integrated shoe soles and orthotics of claim 27, wherein an inner surface and an outer surface of at least two said integrated shoe soles and orthotics of said set are substantially parallel to each other between a position proximate to a lateral sidemost extent and a position proximate to a medial sidemost extent, as viewed in at least one frontal plane cross section when said at least two integrated shoe sole and orthotics of said set are upright and in an unloaded condition.

* * * * *